United States Patent
Govari et al.

(10) Patent No.: US 12,402,962 B2
(45) Date of Patent: Sep. 2, 2025

(54) ROBOT MANIPULATOR FOR EYE SURGERY TOOL

(71) Applicant: JOHNSON & JOHNSON SURGICAL VISION, INC., Irvine, CA (US)

(72) Inventors: Assaf Govari, Haifa (IL); Ilya Sitnitsky, Nahariya (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 348 days.

(21) Appl. No.: 18/081,816

(22) Filed: Dec. 15, 2022

(65) Prior Publication Data

US 2023/0218357 A1  Jul. 13, 2023

Related U.S. Application Data

(60) Provisional application No. 63/297,398, filed on Jan. 7, 2022.

(51) Int. Cl.
| | |
|---|---|
| A61B 34/32 | (2016.01) |
| A61B 90/00 | (2016.01) |
| A61F 9/007 | (2006.01) |

(52) U.S. Cl.
CPC ............ *A61B 34/32* (2016.02); *A61B 90/361* (2016.02); *A61F 9/00745* (2013.01)

(58) Field of Classification Search
CPC ......... A61B 34/20; A61B 34/25; A61B 34/30; A61B 34/32; A61B 34/35; A61B 34/37; A61B 34/70; A61B 34/74; A61B 34/77; A61B 2034/2065; A61B 90/30; A61B 90/36; A61B 90/361; A61B 90/37;
(Continued)

(56) References Cited

U.S. PATENT DOCUMENTS

| | | |
|---|---|---|
| 10,744,035 B2 | 8/2020 | Alvarez et al. |
| 2014/0194859 A1 | 7/2014 | Ianchulev |

(Continued)

FOREIGN PATENT DOCUMENTS

| | | |
|---|---|---|
| WO | 2017100463 A1 | 6/2017 |

OTHER PUBLICATIONS

Bourcier T., et al., "Robot-Assisted Simulated Cataract Surgery," Journal Cataract and Refractive Surgery, May 2017, vol. 43(4), pp. 552-557, XP085033601, ISSN: 0886-3350, DOI: 10. 1016/J.JCRS. 2017.02.020.

(Continued)

*Primary Examiner* — Robert A Lynch

(57) ABSTRACT

An eye surgery apparatus includes an eye surgery tool, an imaging system, a robotic arm, and a processor. The eye surgery tool has a distal end for insertion into an eye of a patient through an incision in the eye. The imaging system is configured to acquire images showing the incision and at least part of the eye surgery tool. The robotic arm is coupled with the eye surgery tool, which is configured to move the distal end of the eye surgery tool inside the eye according to one or more commands issued during an eye surgery. The processor is configured to, during the eye surgery (i) receive the images from the imaging system, (ii) monitor the commands issued to the robotic arm, (iii) detect, by analyzing the images, that a monitored command is expected to enlarge the incision, and (iv) initiate responsive action with respect to the detected command.

14 Claims, 3 Drawing Sheets

(58) Field of Classification Search
CPC ...... A61B 2090/3612; A61B 2090/363; A61B 2090/364; A61B 2090/365; A61B 2090/366; A61B 2090/368; A61F 9/007; A61F 9/00736; A61F 9/00745; A61F 9/00754; A61F 2009/0087; A61F 2009/00872; A61F 2009/00885; A61F 2009/00887
See application file for complete search history.

(56) References Cited

U.S. PATENT DOCUMENTS

2018/0353645 A1* 12/2018 Zhang .................. A61F 9/0008
2022/0079808 A1   3/2022 Gliner et al.

OTHER PUBLICATIONS

Gerber, M.J., Pettenkofer, M. & Hubschman, JP. Advanced robotic surgical systems in ophthalmology. Eye 34, 1554-1562 (2020). https://doi.org/10.1038/s41433-020-0837-9.

* cited by examiner

ROBOT MANIPULATOR FOR EYE SURGERY TOOL

CROSS-REFERENCE TO RELATED APPLICATIONS

This application claims the benefit of U.S. Provisional Patent Application 63/297,398, filed Jan. 7, 2022, whose disclosure is incorporated herein by reference.

FIELD OF THE DISCLOSURE

The present disclosure relates generally to robotic medical systems for eye surgery, and particularly to robotic phacoemulsification systems.

BACKGROUND OF THE DISCLOSURE

An eye surgery may be required in some ophthalmic medical conditions. For example, a physician may recommend cataract removal using phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution to maintain the anterior chamber of the eye. After removing the cataract with phacoemulsification, the softer outer lens cortex is removed with suction. An intraocular lens (IOL) is then introduced into the empty lens capsule restoring the patient's vision.

Various techniques to invasively treat a cataracted eye were proposed in the patent literature. For example, U.S. Pat. No. 10,744,035 describes systems and processes for facilitating the removal of cataract material with a robotically assisted tool with laser, irrigation capabilities, aspiration capabilities. Tool guidance systems that make use of vision technologies, including optical coherence tomography (OCT), white light imaging, and structured light imaging. Emulsification patterns optimized to minimize risk to the patient and reduce procedure time. Robotic tools with articulation capabilities that allow for precise control during capsulorhexis and emulsification procedures. Robotic instrument drive mechanisms combined with pumps, flow meters, and valves regulate and control irrigation and aspiration functionalities during robotic ophthalmologic procedures. Use of a robotically controlled articulating tip may minimize the size of the incision in the lens capsule necessary to extract the cataract material.

DETAILED DESCRIPTION OF EXAMPLES

Overview

Figure 1:
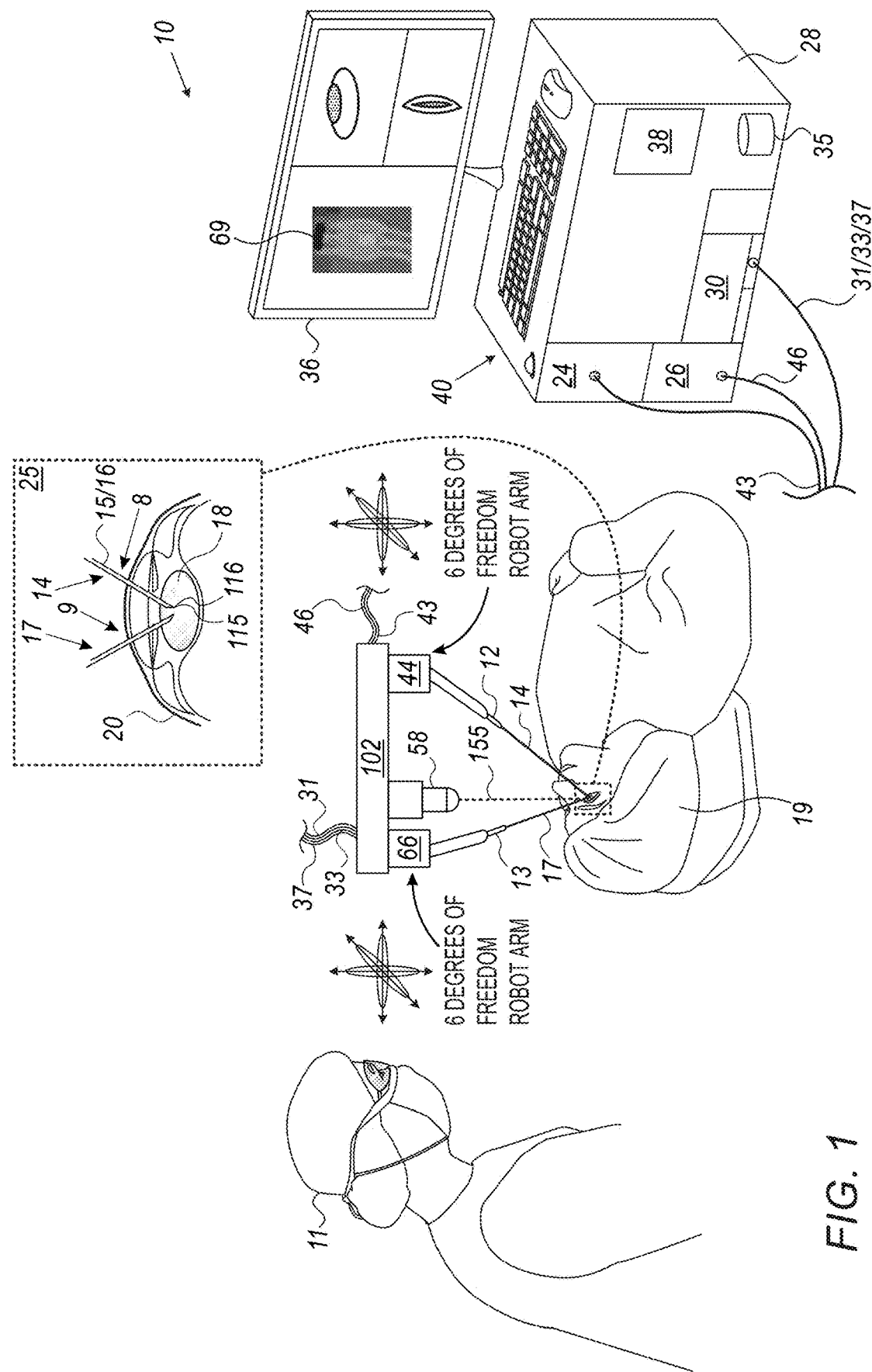
FIG. 1 is a schematic, pictorial view of a phacoemulsification apparatus comprising a phacoemulsification probe coupled to a robotic arm for moving the phacoemulsification probe inside an eye using an incision as a pivot point, in accordance with an example of the present disclosure.

Eye surgery may involve inserting a number of surgical tools into the eye via small incisions made in the surface of the eye. For example, cataract surgery typically requires two incisions in the cornea: one for a phacoemulsification probe, and a second for a different tool such as a curette. The surgeon performing the procedure adjusts movements of the inserted tools in such a way so as not to enlarge the incisions. However, if the tools are operated robotically, there may be no such limitation placed on the robots.

Examples of the present disclosure that are described hereinafter provide a robotic eye surgery apparatus and algorithms to perform eye surgery using tools held by robotic arms of the apparatus while maintaining minimal and stable incision entry points during the procedure.

In some examples, the processor identifies the position of the eye surgery tool relative to the incision, by analyzing images acquired in real-time. Based on the identified position, the processor detects that the command is expected to enlarge the incision. To this end, the coordinates of any incision are identified by image processing (e.g., using edge detection) and the processor can determine if a requested track of the tip (given in a same coordinate system) will comprise the incision.

Typically, a processor of the apparatus instructs the robots to move the distal tips in response to commands the processor receives from a surgeon performing the surgery, which the processor finds will not increase the incision. The command can be alternatively received from a robot that performs the surgery automatically using a suitable algorithm, and in such a case the processor verifies the robot automatic operation does not increase the incision. Alternatively, a treatment plan (e.g., an order of removal of a cataract) is uploaded to the processor so it moves the distal tips (e.g., tips of rigid distal ends) so the distal tips cover a volume of the lens according to the plan. The processor overrides any step in the treatment plan that may increase the incision. For both robotic methods, the means described below ensure that the distal end motions do not cause unwanted enlargement of the incisions.

In one example, two robotic arms, one for the phacoemulsification probe, the other for a second tool, are controlled by the processor, which also controls an imaging system. The imaging system images the incisions made in the eye and the distal tips of the phacoemulsification probe and the tool inside the eye. From the images, the processor determines the locations of the incisions and the distal tips. The processor uses this information to calculate robotic motion of the distal ends (that can be fully rigid, or sufficiently rigid relative to eye tissue) that is safe to tissue near the incision, as further described below.

In an example, before performing any given movement, for example moving the distal tip of the phacoemulsification probe several millimeters in a direction to emulsify the lens, the processor calculates how the requested movement can be made so that the only motion of the phacoemulsification probe at the incision is rotation around the incision, using the incision as a pivot point of the rigid distal end, and/or translation of the distal end into or out of the incision. These types of movements do not enlarge the incision, and so the processor calculates and commands the robotic arm (that has a sufficient number of degrees of freedom) to make only these types of movements.

In another example, the processor overrides any command made by a surgeon that is predicted by the processor calculations to enlarge an incision. Namely, no movement of the rigid distal ends which might enlarge an incision is permitted. In another example, if the surgeon further requests such a movement, the processor warns the surgeon that the request may enlarge the incision.

Using the disclosed apparatuses and methods for robotic eye surgery (e.g., emulsification) may allow more accurate and less hazardous eye surgeries, such as cataract surgeries.

APPARATUS DESCRIPTION

FIG. 1 is a schematic, pictorial view of an eye surgery apparatus 10 comprising robot-mounted eye surgical tools 12 and 13, in accordance with an example of the present disclosure. Surgical tools 12 and 13 are mounted on robot arms 44 and 66, respectively, and have rigid distal ends 14 and 17, respectively, engaging a lens capsule 18 of an eye 20 of a patient 19. The rigid distal ends are inserted via respective incisions 8 and 9 in the cornea of eye 20, the incisions made just before by another tool, e.g., by a physician 11.

In the example shown in inset 25, rigid distal end 14 comprises, by way of example, phacoemulsification probe 12, which itself comprises an aspiration channel 15 and an irrigation channel 16 (which can be coaxial or side-by-side). As shown, aspiration channel 15 has an inlet 115, and irrigation channel 16 has an outlet 116, both at a distal tip of phacoemulsification probe 12, from which cataract fragments are aspirated and into which replenishing irrigation fluid flows, respectively. Rigid distal end 14 is shown straight, though it may be curved or bent. Rigid distal end 17 is of another surgical tool (13), for example a curette.

Figure 2:
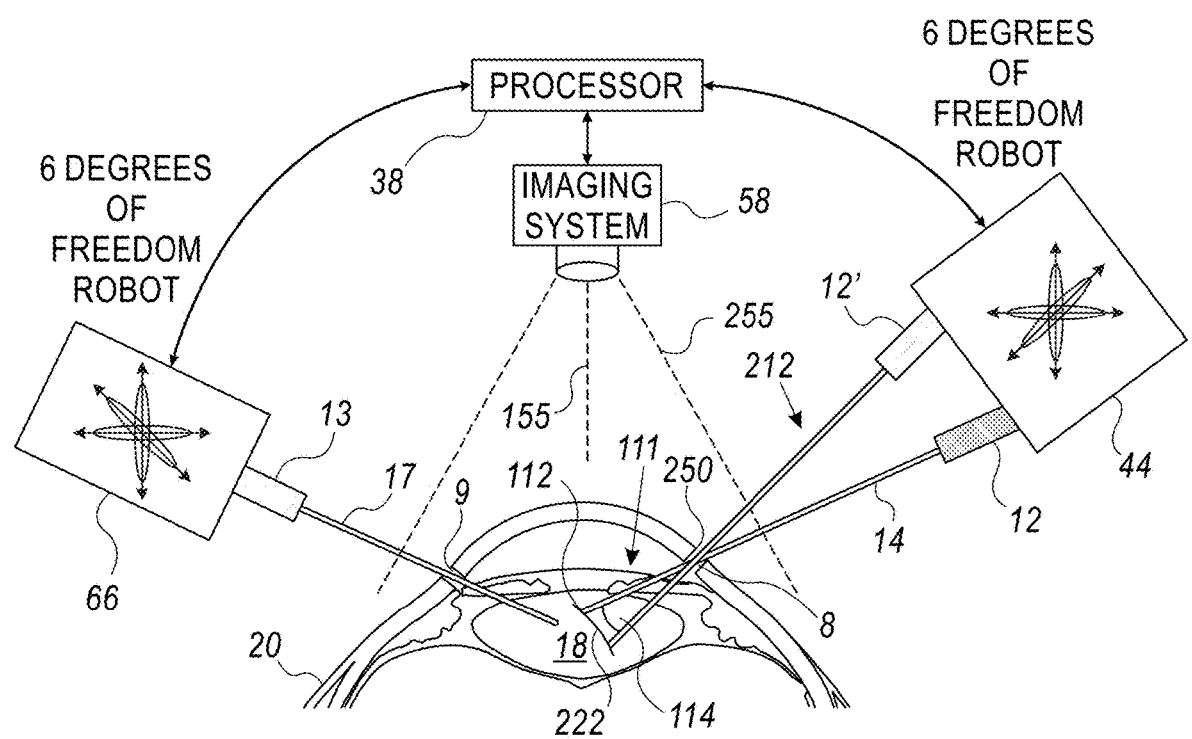
FIG. 2 is a block diagram schematically illustrating the operation of the apparatus of FIG. 1 using an incision as a pivot point for the phacoemulsification probe, in accordance with an example of the present disclosure.

Robotic arms 44 and 66 (mounted on a base 102) are configured to, at minimum, tilt directions of respective distal ends 14 and 17 within lens capsule 18, and adjust a depth of the distal ends inside the eye, while maintaining axes, or pivots, of distal ends 14 and 17 at respective incisions 8 and 9 in eye 20, so as not to enlarge incisions 8 and 9, as described in FIG. 2. While the shown example uses robotic arms 44 and 66, each having six degrees of freedom, the number of degrees of freedom may vary with design, to maintain the aforementioned axes at incisions 8 and 9 while the distal tips of rigid distal ends 14 and 17 move inside eye 20.

In the exemplified example, during the phacoemulsification procedure robotic arm 44 moves rigid distal end 14 so that aspiration inlet 115 and irrigation outlet 116 follow a path (shown in FIG. 2) inside the eye, according to, for example, commands from a processor 38 communicated via a cable 31, that implements a treatment plan (e.g., one stored in a memory 35) made by physician 11. Similarly, robotic arm 66 moves rigid distal end 17 according to commands from processor 38 communicated via a cable 33, typically in a coordinated track with that of rigid distal end 17.

In the shown example, console 28 comprises a piezoelectric drive module 30, which is coupled, using electrical wiring running in cable 37, with a piezoelectric crystal inside probe 12 that generates vibration of rigid distal end 14 that breaks cataracted lens 18. Drive module 30 is controlled by processor 38 to adjust a vibration power and/or duration and/or frequency.

During the phacoemulsification procedure, a pumping subsystem 24 comprised in a console 28 pumps irrigation fluid from an irrigation reservoir to outlet 116 to irrigate the eye. In an example, the irrigation fluid may be administered via a gravity-fed method or any other known method in the art. The fluid is pumped via a tubing line 43 running from the console 28 to phacoemulsification probe 12. Eye fluid and waste matter (e.g., emulsified parts of the cataract) are aspirated via inlet 115 to a collection receptacle (not shown) by a pumping subsystem 26 also comprised in console 28 and using a tubing line 46 running from phacoemulsification probe 12 to console 28.

In the shown example, apparatus 10 further comprises an eye imaging system 58 mounted on base 102, e.g., a video camera with an optical imaging axis 155, the camera capturing an image (e.g., records video images) of the aforementioned incisions 8 and 9, and of lens capsule 18, both in real time, including the inserted rigid distal ends. The captured image 69 is displayed on a display 36. Real time image processing enables processor 38 to calculate the required motions of robotic arms 44 and 66, so as to perform the eye surgery without enlarging eye incisions 8 and 9, or to override surgeon's 11 commands that may cause enlargement of an incision, as described below.

Processor 38 presents other results of the cataract removal procedure on display 36. Processor 38 may receive user-based commands via a user interface 40, which may include setting or adjusting an irrigation rate and/or aspiration rate. User interface 40 may be combined with a touch screen graphical user interface of display 36.

Some or all of the functions of processor 38 may be combined in a single physical component or, alternatively, implemented using multiple physical components. These physical components may comprise hard-wired or programmable devices, or a combination of the two. In some examples, at least some of the functions of processor 38 may be carried out by suitable software stored in memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

The apparatus shown in FIG. 1 may include further elements, which are omitted for clarity of presentation. For example, physician 11 may hold a control handle with which the physician can, for example, abort the automatic procedure. Physician 11 may apply medications with another tool, which is also not shown in order to maintain clarity and simplicity of presentation.

While the exemplified surgical procedure involves corneal incisions, incisions may be performed at other eye locations, depending on the type of eye surgery. Enlarging incisions in such other locations (e.g., at the sclera) would similarly need to be minimized during the surgery, to prevent damage to the eye. While FIG. 1 refers to eye surgical tools, the technique can also be used with eye diagnostic devices (e.g., a miniature camera, illuminator, pressure and/or temperature sensors, among others) fitted at a distal portion of a rigid distal end for insertion into the eye.

Robot Manipulators for Eye Tools

FIG. 2 is a block diagram schematically illustrating the operation of apparatus 10 of FIG. 1 using incision 8 as a pivot point for phacoemulsification probe 12, in accordance with an example of the present disclosure.

As seen, rigid distal ends 14 and 17 of respective probe 12 and tool 13 are located partially inside eye 20, accessing the eye via incisions 8 and 9. Probe 12 and tool 13 are coupled to respective robotic arms 44 and 66 to perform an operation inside lens capsule 18, such as phacoemulsification (using probe 12) and curetting (using tool 13). To this end, by way of example, a distal portion 111 of distal rigid end 14 is inside the eye, with portion 111 length measured between a pivot point 250 at incision 8 and a tip 112 of rigid distal end 14.

Assuming tip 112 is required to follow a path 222, processor 38 calculates the movement required by robotic arm 44 and instructs the robotic arm to move tip 112 along path 222 by changing only a pivot angle 114 and length of distal portion 111 within the eye. In this way, incision 8 is not enlarged by the required motion. As illustrated by layout 212, the robotic arm moves the probe (now designated 12') to a new position and orientation such that rigid distal end 14 goes through the same pivot point 250 to a new location over path 222 (i.e., by having a different angle and portion length).

Processor 38 calculates the required motion using information from imaging system 58 that can be a video camera with an optical imaging axis 155 and field of view (FOV) 255. A video camera of imaging system 58 captures at least part of the eye, including incisions 8 and 9 and the distal tips (e.g., tip 112) of the phacoemulsification probe and the curetting tool, and from these images the processor determines if and how to move the distal tips.

The example apparatus shown in FIG. 2 is chosen purely for the sake of conceptual clarity. For example, the rigid distal ends may be curved or bent. As another example, imaging system 58 may include built-in image processing circuitries to perform the required image processing.

Figure 3:
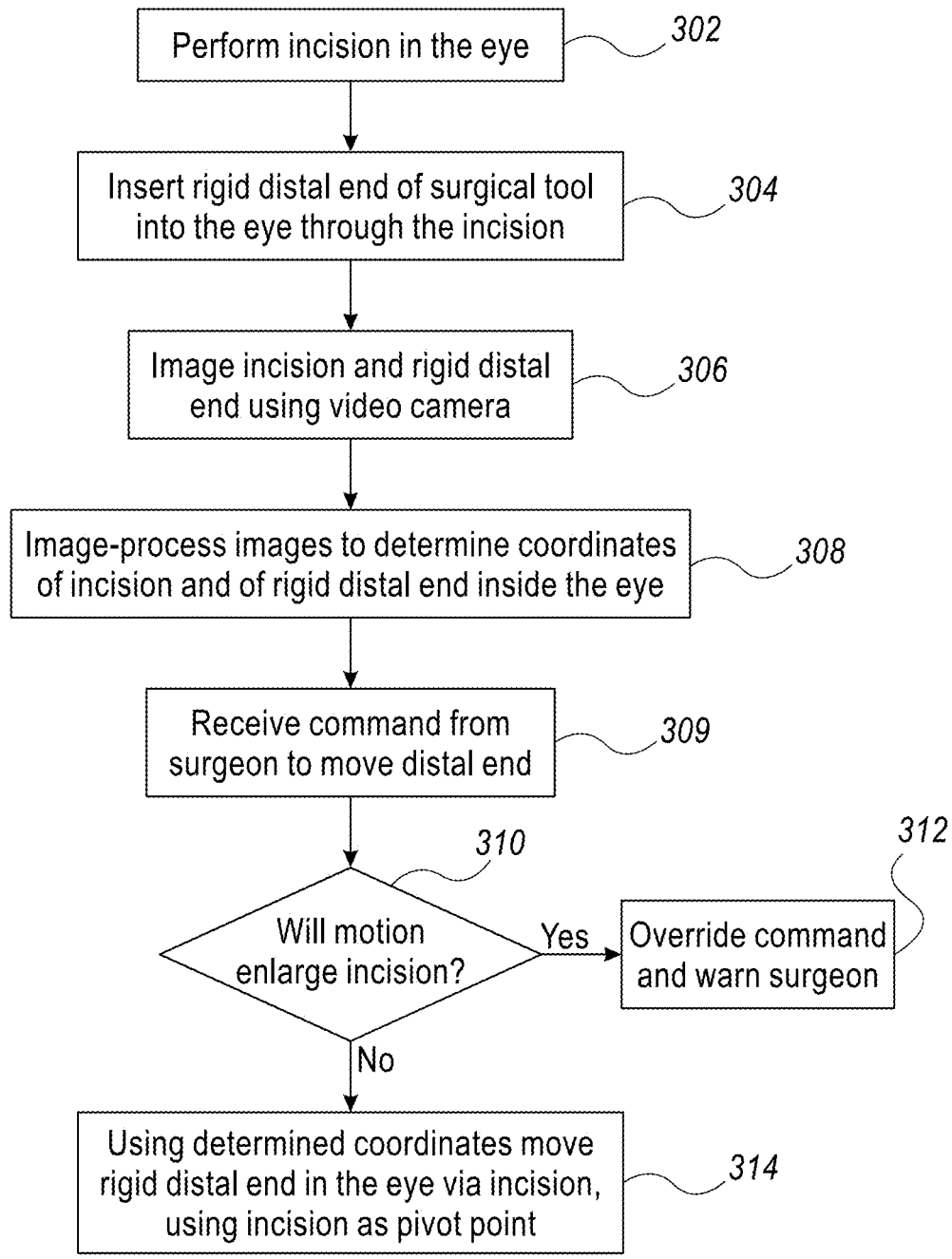
FIG. 3 is a flow chart schematically illustrating an incision pivot point operating method of the apparatus of FIG. 1, in accordance with an example of the present disclosure.

FIG. 3 is a flow chart schematically illustrating an incision pivot point operating method of apparatus 10 of FIG. 1, in accordance with an example of the present disclosure. The algorithm, according to the presented example, carries out a process that begins with physician 11 operating apparatus 10 (e.g., processor 38) to command robotic arm 44 to have a surgical tool, such as diamond tipped knife perform the incision (e.g., incision 8) in eye 20, at an eye incision step 302. Alternatively, the incision may be performed manually by physician 11, using, for example, a scalpel or another type of blade.

At a distal end insertion step 304, processor 38 commands robotic arm 44 to have tool 12 insert a distal portion 111 of rigid distal end 14 through incision 6 into a predetermined location inside eye 20.

At imaging step 306, imaging system 58 images incision 8 and tip 112 of rigid distal end 14.

Processor 38 receives the images and perform image processing to determine coordinates of incision 8 and tip 112 of rigid distal end 14 inside eye 20, at an image processing step 308.

The processor receives a command from surgeon 11 at a command receiving step 309, to move rigid distal end 14 inside eye 20 to, for example, perform phacoemulsification at a new location in lens 18.

Processor 38 monitors the commands issued by the surgeon to the robotic arm, to check if a monitored command is expected to enlarge the incision. To this end, processor 38 analyzes the images processed in step 308. Using the coordinates determined in step 308, processor 38 calculates the required motion of rigid distal end 14 and checks if the motion will enlarge incision 8, at a checking step 310.

If the answer is yes, processor 38 initiates a responsive action with respect to the monitored and detected potentially hazardous tip moving command, e.g., responsive action such as overriding the command and providing an audio and/or visual warning to physician 11, at a command overriding step 312.

In some examples, the processor is configured to block the detected command from being executed by the robotic arm and/or to output an alert to the surgeon with respect to the detected command.

If the answer is no, processor 38 instructs robotic arm 44 to move rigid distal end 14 inside eye 20 over a path as required by the commanded step (e.g., to follow track 222) while maintaining incision 8 as a pivot point of the motion of the distal end, at tool operation step 314.

The example flow chart shown in FIG. 3 is chosen purely for the sake of conceptual clarity. For example, as described above, additional tools may be inserted via different incisions in the eye.

Example 1

An eye surgery apparatus (10), comprising (a) an eye surgery tool (12, 13) having a distal end (14, 17) for insertion into an eye (20) of a patient (19) through an incision (8, 9) in the eye, (b) an imaging system (58), which is configured to acquire images (69) showing the incision (8, 9) and at least part of the eye surgery tool (12, 13), (c) a robotic arm (44, 66) coupled with the eye surgery tool (12, 13), which is configured to move the distal end (14, 17) of the eye surgery tool (12, 13) inside the eye (20) according to one or more commands issued during an eye surgery, and (d) a processor (38), which is configured to, during the eye surgery (i) receive the images (69) from the imaging system (58), (ii) monitor the commands issued to the robotic arm (44, 66), (iii) detect, by analyzing the images (69), that a monitored command is expected to enlarge the incision (8, 9), and (iv) initiate a responsive action with respect to the detected command.

Example 2

The eye surgery apparatus according to example 1, wherein the one or more commands are issued by one of a surgeon and an algorithm that the robotic arm (44, 66) executes.

Example 3

The eye surgery apparatus according to example 1 or 2, wherein the processor (38) is configured to identify a position of the at least part of the eye surgery tool (12, 13), relative to the incision (8, 9), by analyzing the images (69), and to detect, based on the identified position, that the command is expected to enlarge the incision (8, 9).

Example 4

The eye surgery apparatus according to example 1 or 2, wherein the processor (38) is configured to block the detected command from being executed by the robotic arm (44, 66).

Example 5

The eye surgery apparatus according to example 1 or 2, wherein the processor (38) is configured to output an alert to a surgeon with respect to the detected command.

Example 6

The eye surgery apparatus according to any one of examples 1-5, wherein the eye surgery is a phacoemulsification procedure, the eye surgery tool is a phacoemulsification probe (12), and the imaging system (58) is configured to image a tip (112) of the phacoemulsification probe (12).

Example 7

The eye surgery apparatus according to any one of examples 1-7, wherein the imaging system (58) comprises a video camera, and wherein the images (69) comprise video images.

Example 8

An eye surgery method, comprising (a) inserting a distal end of an eye surgery tool into an eye of a patient through an incision in the eye, (b) using an imaging system, acquiring images showing the incision and at least part of the eye surgery tool, (c) using a robotic arm, moving the distal end of the eye surgery tool inside the eye according to one or more commands issued to the robotic arm, (d) receiving the images from the imaging system, (e) monitoring the commands issued to the robotic arm, (f) detecting, by analyzing the images, that a monitored command is expected to enlarge the incision, and (g) initiating a responsive action with respect to the detected command.

Although the examples described herein mainly address eye surgeries, and cataract surgeries in particular, the methods described herein can also be used in other minimally invasive surgical applications at other body locations (e.g., via skin or skull) using rigid tools having access via small incisions that require protection from enlargement.

It will be thus appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An eye surgery apparatus, comprising:
   an eye surgery tool having a distal end for insertion into an eye of a patient through an incision in the eye;
   an imaging system, which is configured to acquire images showing the incision and at least part of the eye surgery tool;
   a robotic arm coupled with the eye surgery tool, which is configured to move the distal end of the eye surgery tool inside the eye according to one or more commands issued during an eye surgery; and
   a processor, which is configured to, during the eye surgery:
   receive the images from the imaging system;
   monitor the commands issued to the robotic arm;
   detect, by analyzing the images, that a monitored command is expected to enlarge the incision; and
   initiate a responsive action with respect to the detected command.

2. The eye surgery apparatus according to claim 1, wherein the one or more commands are issued by one of a surgeon and an algorithm that the robotic arm executes.

3. The eye surgery apparatus according to claim 1, wherein the processor is configured to identify a position of the at least part of the eye surgery tool, relative to the incision, by analyzing the images, and to detect, based on the identified position, that the command is expected to enlarge the incision.

4. The eye surgery apparatus according to claim 1, wherein the processor is configured to block the detected command from being executed by the robotic arm.

5. The eye surgery apparatus according to claim 1, wherein the processor is configured to output an alert to a surgeon with respect to the detected command.

6. The eye surgery apparatus according to claim 1, wherein the eye surgery is a phacoemulsification procedure, the eye surgery tool is a phacoemulsification probe, and the imaging system is configured to image a tip of the phacoemulsification probe.

7. The eye surgery apparatus according to claim 1, wherein the imaging system comprises a video camera, and wherein the images comprise video images.

8. An eye surgery method, comprising:
   inserting a distal end of an eye surgery tool into an eye of a patient through an incision in the eye;
   using an imaging system, acquiring images showing the incision and at least part of the eye surgery tool;
   using a robotic arm, moving the distal end of the eye surgery tool inside the eye according to one or more commands issued to the robotic arm;
   receiving the images from the imaging system;
   monitoring the commands issued to the robotic arm;
   detecting, by analyzing the images, that a monitored command is expected to enlarge the incision; and
   initiating a responsive action with respect to the detected command.

9. The eye surgery method according to claim 8, wherein the one or more of commands are issued by one of a surgeon and an algorithm that the robotic arm executes.

10. The eye surgery method according to claim 8, wherein detecting that the monitored command is expected to enlarge the incision comprises identifying a position of the at least part of the eye surgery tool, relative to the incision, by analyzing the images, and detecting, based on the identified positions, that the command is expected to enlarge the incision.

11. The eye surgery method according to claim 8, wherein initiating the responsive action comprises blocking the detected command from being executed by the robotic arm.

12. The eye surgery method according to claim 8, wherein initiating the responsive action comprises outputting an alert to the surgeon with respect to the detected command.

13. The eye surgery method according to claim 8, wherein the eye surgery is a phacoemulsification procedure, the eye surgery tool is a phacoemulsification probe, and the imaging system is configured to image a tip of the phacoemulsification probe.

14. The eye surgery method according to claim 8, wherein the imaging system comprises a video camera, and wherein the images comprise video images.

* * * * *